US 6,651,658 B1

(12) United States Patent
Hill et al.

(10) Patent No.: US 6,651,658 B1
(45) Date of Patent: *Nov. 25, 2003

(54) PORTABLE OXYGEN CONCENTRATION SYSTEM AND METHOD OF USING THE SAME

(75) Inventors: Theodore B. Hill, San Diego, CA (US); Edward A. Radtke, El Cajon, CA (US); Robert A. Schneider, Del Mar, CA (US); James A. Bixby, La Jolla, CA (US)

(73) Assignees: SeQual Technologies, Inc., San Diego, CA (US); Teijin Limited, Osaka (JP)

( * ) Notice: Subject to any disclaimer, the term of this patent is extended or adjusted under 35 U.S.C. 154(b) by 212 days.

This patent is subject to a terminal disclaimer.

(21) Appl. No.: 09/632,099

(22) Filed: Aug. 3, 2000

(51) Int. Cl.[7] .......................... A61M 16/00; A62B 7/00; F16K 31/02
(52) U.S. Cl. .......................... 128/204.23; 128/204.18; 128/204.26; 128/204.22; 128/205.11
(58) Field of Search ............... 128/201.25, 205.11, 128/205.18, 204.22, 204.21, 202.26, 205.12; 55/26, 62, 18, 179, 204.18, 204.23, 204.26

(56) References Cited

U.S. PATENT DOCUMENTS

| 4,077,779 A |   | 3/1978  | Sircar             |
| 4,469,494 A |   | 9/1984  | Van Weenen         |
| 4,477,264 A |   | 10/1984 | Kratz et al.       |
| 4,491,459 A |   | 1/1985  | Pinkerton          |
| 4,648,397 A | * | 3/1987  | Beale ........ 128/204.26 |
| 4,801,308 A |   | 1/1989  | Keefer             |
| 4,826,510 A | * | 5/1989  | McCombs ...... 128/204.18 |
| 4,859,217 A |   | 8/1989  | Chao               |
| 4,925,464 A |   | 5/1990  | Rabenau et al.     |
| 4,968,329 A |   | 11/1990 | Keefer             |
| 4,971,609 A |   | 11/1990 | Pawlos             |
| 5,074,892 A |   | 12/1991 | Leavitt            |
| 5,112,367 A |   | 5/1992  | Hill               |
| 5,114,441 A |   | 5/1992  | Kanner et al.      |
| 5,226,410 A | * | 7/1993  | Fournol ........ 128/202.11 |
| 5,268,021 A |   | 12/1993 | Hill et al.        |
| 5,365,922 A | * | 11/1994 | Raemer ........ 128/202.22 |
| 5,366,541 A |   | 11/1994 | Hill et al.        |
| 5,413,625 A |   | 5/1995  | Chao et al.        |
| RE35,099 E  |   | 11/1995 | Hill               |
| 5,495,848 A | * | 3/1996  | Aylsworth et al. ...... 128/204.23 |
| 5,593,478 A |   | 1/1997  | Hill et al.        |
| 5,626,151 A |   | 5/1997  | Linden             |
| 5,706,801 A | * | 1/1998  | Remes et al. ...... 128/202.22 |
| 5,730,778 A |   | 3/1998  | Hill et al.        |
| 5,807,423 A |   | 9/1998  | Lemcoff et al.     |
| 5,814,130 A |   | 9/1998  | Lemcoff et al.     |

(List continued on next page.)

FOREIGN PATENT DOCUMENTS

| EP | 0 266 051 A1 | 9/1987 |
| GB | 2 164 568 A  | 3/1986 |
| WO | WO 97/32692  | 9/1997 |

*Primary Examiner*—Weilun Lo
*Assistant Examiner*—Michael Mendoza
(74) *Attorney, Agent, or Firm*—Procopio, Cory, Hargreaves & Savitch, LLP

(57) ABSTRACT

The present invention is directed to a portable oxygen concentrator system adapted to be transported by a user. The portable oxygen concentrator system includes an energy source, an air separation device powered by the energy source and adapted to convert ambient air into concentrated oxygen gas for the user, at least one sensor adapted to sense one or more conditions indicative of the oxygen gas needs of the user, and a control unit interrelated with the air separation device and the at least one sensor to control the air separation device so as to supply an amount of oxygen gas equivalent to the oxygen gas needs of the user based at least in part upon the one or more conditions sensed by the at least one sensor.

72 Claims, 4 Drawing Sheets

U.S. PATENT DOCUMENTS

| | | | |
|---|---|---|---|
| 5,814,131 A | | 9/1998 | Lemcoff et al. |
| 5,820,656 A | | 10/1998 | Lemcoff et al. |
| 5,827,358 A | | 10/1998 | Kulish et al. |
| 5,848,591 A | * | 12/1998 | Weismann ............. 128/203.12 |
| 5,874,897 A | * | 2/1999 | Klempau et al. ............ 128/903 |
| 5,890,490 A | | 4/1999 | Aylsworth et al. |
| 5,891,217 A | | 4/1999 | Lemcoff et al. |
| 5,893,944 A | | 4/1999 | Dong |
| 5,912,422 A | | 6/1999 | Bomard et al. |
| 5,928,189 A | | 7/1999 | Phillips |
| 5,931,159 A | * | 8/1999 | Suzuki et al. .......... 128/204.18 |
| 5,975,081 A | * | 11/1999 | Hood et al. ................ 128/845 |
| 5,988,165 A | * | 11/1999 | Richey et al. ......... 128/204.22 |
| 6,000,395 A | * | 12/1999 | Brown ................. 128/201.29 |
| 6,001,057 A | * | 12/1999 | Bongiovanni et al. ........ 600/21 |
| 6,010,317 A | | 1/2000 | Maget |
| 6,010,555 A | | 1/2000 | Smolarek et al. |
| 6,028,514 A | * | 2/2000 | Lemelson et al. .......... 128/903 |
| 6,050,940 A | * | 4/2000 | Braun et al. ................ 128/920 |
| 6,051,050 A | | 4/2000 | Keefer et al. |
| 6,056,804 A | | 5/2000 | Keefer et al. |
| 6,068,680 A | | 5/2000 | Kulish et al. |
| 6,143,056 A | | 11/2000 | Smolarek et al. |
| 6,152,135 A | * | 11/2000 | DeVries et al. ........ 128/204.18 |
| 6,152,991 A | | 11/2000 | Ackley |
| 6,176,897 B1 | | 1/2001 | Keefer |
| 6,253,778 B1 | | 7/2001 | Smolarek et al. |
| 6,302,107 B1 | * | 10/2001 | Richey et al. ......... 128/205.11 |
| 6,346,139 B1 | * | 2/2002 | Czabala ..................... 95/130 |
| 6,349,724 B1 | * | 2/2002 | Burton et al. .......... 128/204.18 |
| 6,401,487 B1 | * | 6/2002 | Kotliar ........................ 62/640 |
| 2001/0023640 A1 | | 9/2001 | Keefer et al. |

* cited by examiner

PORTABLE OXYGEN CONCENTRATION SYSTEM AND METHOD OF USING THE SAME

BACKGROUND OF THE INVENTION

The field of this invention relates, in general, to oxygen concentrators and, in particular, to portable oxygen concentration systems for ambulatory respiratory patients that allow them to lead normal and productive lives.

There is a burgeoning need for home and ambulatory oxygen. Supplemental oxygen is necessary for patients suffering from lung disorders; for example, pulmonary fibrosis, sarcoidosis, or occupational lung disease. For such patients, oxygen therapy is an increasingly beneficial, life-giving development. While not a cure for lung disease, supplemental oxygen increases blood oxygenation, which reverses hypoxemia. This therapy prevents long-term effects of oxygen deficiency on organ systems—in particular, the heart, brain and kidneys. Oxygen treatment is also prescribed for Chronic Obstructive Pulmonary Disease (COPD), which afflicts about six-hundred million people in the U.S., and for other ailments that weaken the respiratory system, such as heart disease and AIDS. Supplemental oxygen therapy is also prescribed for asthma and emphysema.

The normal prescription for COPD patients requires supplemental oxygen flow via nasal cannula or mask twenty four hours per day. The average patient prescription is two liters per minute of high concentration oxygen to increase the oxygen level of the total air inspired by the patient from the normal 21% to about 40%. While the average oxygen flow requirement is two liters per minute, the average oxygen concentrator has a capacity of four to six liters of oxygen per minute. This extra capacity is occasionally necessary for certain patients who have developed more severe problems, are not generally able to leave the home (as ambulatory patients), and do not require a portable oxygen supply.

There are currently three modalities for supplemental medical oxygen: high pressure gas cylinders, cryogenic liquid in vacuum insulated containers or thermos bottles commonly called "dewars", and oxygen concentrators. Some patients require in-home oxygen only while others require in-home as well as ambulatory oxygen depending on their prescription. All three modalities are used for in-home use, although oxygen concentrators are preferred because they do not require dewar refilling or exchange of empty cylinders with full ones. Home oxygen concentrators, however, do have their drawbacks. They consume relatively large amounts of electricity (350–400 Watts), are relatively large (about the size of a night stand), are relatively heavy (weight about 50 lbs.), emit quite a bit of heat, and are relatively noisy.

Only small high pressure gas bottles and small liquid dewars are truly portable enough to be used for ambulatory needs (outside the home). Either modality may be used for both in-home and ambulatory use or may be combined with an oxygen concentrator which would provide in-home use.

As described below, the current oxygen-supplying methods and devices have proven cumbersome and unwieldy and there has been a long-felt need for an improved portable device for supplying oxygen to the user.

For people who need to have oxygen and operate away from an oxygen-generating or oxygen-storage source such as a stationary oxygen system (or even a portable system which cannot be readily transported), the two most prescribed options generally available to patients are: (a) to carry with them small cylinders typically in a wheeled stroller; and (b) to carry portable containers typically on a shoulder sling. Both these gaseous oxygen and liquid oxygen options have substantial drawbacks, but from a medical view, both have the ability to increase the productive life of a patient.

The major drawback of the gaseous oxygen option is that the small cylinders of gaseous oxygen can only provide gas for a short duration. Another drawback is that a patient's high-pressure gaseous oxygen cylinders are not allowed in some locations such as airplanes because of safety considerations. A further drawback of the gaseous oxygen option is the refill requirement for oxygen once the oxygen has been depleted from the cylinder. These small gas cylinders must be picked up and refilled by the home care provider at a specialized facility. This requires regular visits to a patient's home by a provider and a substantial investment in small cylinders by the provider because so many are left at the patient's home and refilling facility. Although it is technically possible to refill these cylinders in the patient's home using a commercial oxygen concentrator that extracts oxygen from the air, this task would typically require an on-site oxygen compressor to boost the output pressure of the concentrator to a high level in order to fill the cylinders. Some disadvantages of common on-site oxygen compressors are that they are expensive, loud and emit a lot of heat. Additionally, attempting to compress the oxygen in pressurized canisters in the home is potentially dangerous, especially for untrained people. This approach of course presents several safety concerns for in-home use. For example, in order to put enough of this gas in a portable container, it must typically be compressed to high pressure (~2000 psi). Compressing oxygen from 5 psi (the typical output of an oxygen concentrator) to 2000 psi will produce a large amount of heat. (Enough to raise the temperature 165 degrees C per stage based on three adiabatic compression stages with intercooling.) This heat, combined with the oxygen which becomes more reactive at higher pressures, sets up a potential combustion hazard in the compressor in the patient's home. Thus, operation of a high-pressure gas system in the patient's home is dangerous and not a practical solution.

The convenience and safety issues are not the only drawbacks of this compressed oxygen approach. Another drawback is that the compressors or pressure boosters needed are costly because they require special care and materials needed for high pressure oxygen compatibility.

Turning now to the liquid oxygen storage option, its main drawback is that it requires a base reservoir—a stationary reservoir base unit within the patient's home about the size of a standard beer keg—which may be refilled about once a week from an outside source. Liquid oxygen can then be transferred from the patient's base unit to a portable dewar, which can be used by the ambulatory patient. Also, with the liquid oxygen option, there is substantial waste, as a certain amount of oxygen is lost during the transfer to the portable containers and from evaporation. It is estimated that 20% of the entire contents of the base cylinder will be lost in the course of two weeks because of losses in transfer and normal evaporation. These units will typically boil dry over a period of 30 to 60 days even if no oxygen is withdrawn. Home refilling systems that produce liquid oxygen and have the capability of refilling portable liquid oxygen dewars have been proposed. However, these devices require the user to perform the task of refilling bottles and add tens of dollars per month to the user's electric bill, which is not reimbursable.

There are other complications with these portable high-pressure cylinders and liquid dewars. Typically, supplemental oxygen is supplied to the patient by a home care provider, in exchange for which the provider receives a fixed monetary payment from insurance companies or Medicare regardless of the modality. Oxygen concentrators are preferred by the provider as the least expensive option for supplying the patient's at-home needs. For outside the home use, however, only small high-pressure gas bottles and small liquid dewars are portable enough to be used for ambulatory needs. Either one of these two modalities may be used for both in-home and ambulatory use or may be combined with an oxygen concentrator, which would provide in-home use. In either case, the home care provider must make costly weekly or biweekly trips to the patient's home to replenish the oxygen. One of the objects of this invention is to eliminate these costly "milk runs."

So-called "portable" oxygen concentrators are commercially available for providing patients with gaseous oxygen by converting ambient air into concentrated gaseous oxygen. However, these devices are only "portable" in the sense that they are capable of being transported to another point of use via an automobile or an airplane. One of these devices is packaged in a suitcase and is billed as a transportable machine rather than a truly portable oxygen concentrator. The device weighs about 37 lbs. without battery and requires 135 Watts of power at a 2 LPM (liters per minute) oxygen flow rate. Operation from an automobile battery is possible when in route in a car, but operation from a separate battery is impractical. Another device is a 3 LPM concentrator mounted on its own cart. It weighs 22 lbs. without battery and also requires about 135 Watts of power. A further device weighs about 28 lbs. without battery and has a similar flow rate and power requirements to the above devices. Even without a battery, these devices are too heavy for the average ambulatory respiratory patient. With the weight of a battery, these prior art devices are not "portable" in the true sense of the word because they can not be readily transported from one point to another. Because these devices have relatively large power consumption requirements, they also require a sizable battery.

Further, in addition to the weight and power consumption problems with the above oxygen concentrators, none of these prior art concentrators are particularly quiet. They produce noise levels similar to those produced by a home concentrator. In fact, one of these devices specifies noise production at 60 dBA (decibels), about twice the noise of a home concentrator. Consequently, none of these so-called "portable" oxygen concentrators are suitable for use in environments where low noise is especially important, e.g., restaurants, libraries, churches and theatres.

Thus, a long-felt need exists for a truly "portable" oxygen concentration system that eliminates the need for high-pressure gas cylinders and liquid dewars, the constant refilling/replacing requirements associated with high-pressure gas cylinders and liquid dewars, and the need for a separate home oxygen concentration system for ambulatory respiratory patients. A truly "portable" oxygen concentration system would be light enough so that, even with a battery, an average ambulatory respiratory patient could carry the device. Inherently the device would have to be designed to have relatively low power consumption requirements so that a light-weight battery pack or other energy source could be used. Further, the device should be small enough so that it can be conveniently carried by the user, emit a relatively low amount of noise and should only emit a small amount of heat.

SUMMARY OF INVENTION

An aspect of present invention involves a portable oxygen concentrator system adapted to be readily transported by a user. The portable oxygen concentrator system includes an energy source, an air separation device powered by the energy source and adapted to convert ambient air into concentrated oxygen gas for the user, at least one sensor adapted to sense one or more conditions indicative of the oxygen gas needs of the user, and a control unit interrelated with the air separation device and the at least one sensor to control the air separation device so as to supply an amount of oxygen gas equivalent to the oxygen gas needs of the user based at least in part upon the one or more conditions sensed by the at least one sensor.

An additional aspect of the present invention involves a method of supplying gaseous oxygen to a user using a portable oxygen concentrator system adapted to be readily transported by the user. The method includes sensing one or more conditions indicative of the oxygen gas needs of the user with at least one sensor, and controlling an air-separation device to convert ambient air into concentrated oxygen gas and supply an amount of concentrated oxygen gas equivalent to the oxygen gas needs of the user based upon the one or more conditions sensed by the at least one sensor.

Other and further objects, features, aspects, and advantages of the present inventions will become better understood with the following detailed description of the accompanying drawings.

DETAILED DESCRIPTION OF THE PREFERRED EMBODIMENT

I. Portable Oxygen Concentration System

Figure 1:
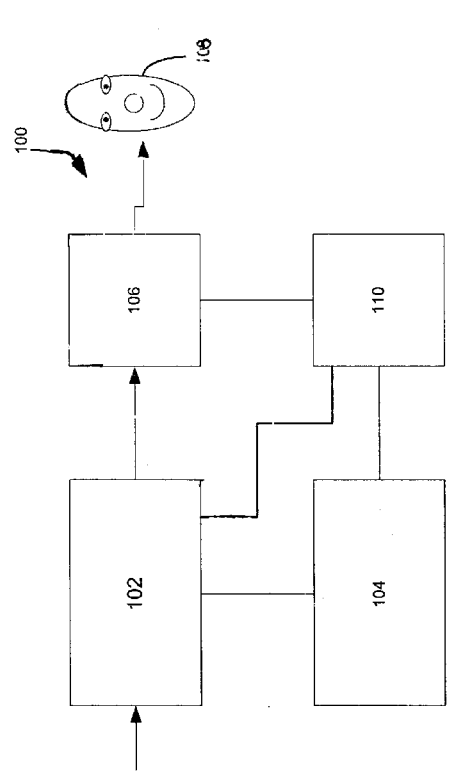
FIG. 1 is a block diagram of a portable oxygen concentration system constructed in accordance with an embodiment of the invention.

With reference to FIG. 1, a portable oxygen concentration system, indicated generally by the reference numeral 100, constructed in accordance with an embodiment of the invention will now be described. The oxygen concentration system 100 includes an air-separation device such as an oxygen gas generator 102 that separates concentrated oxygen gas from ambient air, an energy source such as rechargeable battery, battery pack, or fuel cell 104 that powers at least a portion of the oxygen gas generator 102, one or more output sensors 106 used to sense one or more conditions of the user 108, environment, etc. to determine the oxygen output needed by the user or required from the system 100, and a control unit 110 linked to the output sensor 106, the air separation device 102, and the energy source 104 to control the operation of the air separation device 102 in response to the one or more conditions sensed by the one or more output sensors 106.

In an alternative embodiment, the system 100 may not include the one or more output sensors 106 coupled to the control unit 110. In this embodiment, conditions of the system 100 such as flow rate, oxygen concentration level, etc. may be constant for the system or may be manually controllable. For example, the system 100 may include a user interface 111 (FIG. 5) that allows the user, provider, doctor, etc. to enter information, e.g., prescription oxygen level, flow rate, etc. to control the oxygen output of the system 100.

Each element of the system 100 will now be described in more detail.

A. Air Separation Device

Figure 2:
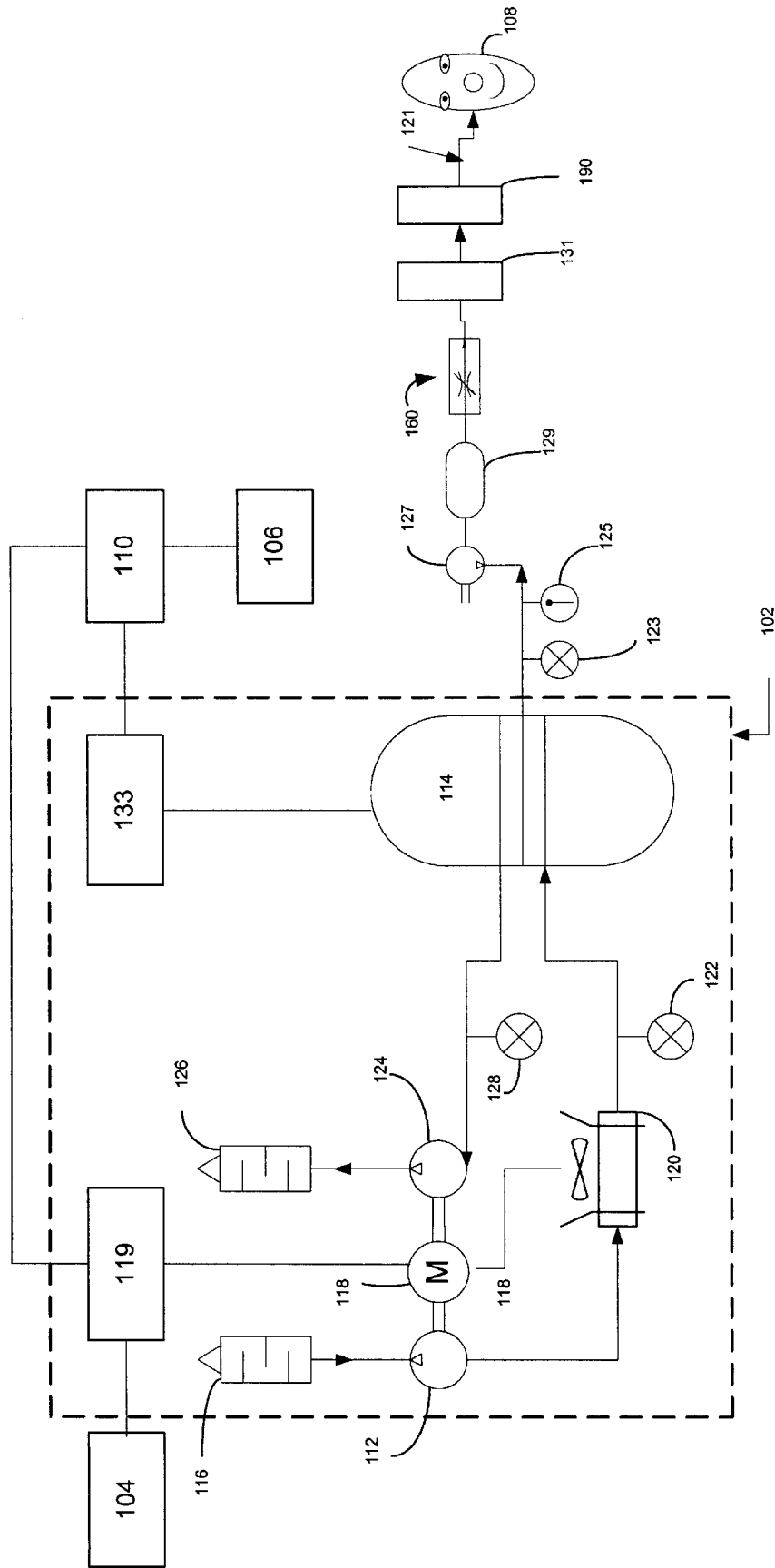
FIG. 2 is a block diagram of a portable oxygen concentration system constructed in accordance with another embodiment of the invention, and illustrates, in particular, an embodiment of an air separation device.

With reference to FIG. 2, the air separation device is preferably an oxygen generator 102 generally including a pump such as a compressor 112 and an oxygen concentrator 114 (OC), which may be integrated.

The oxygen generator 102 may also include one or more of the elements described below and shown within the segmented boundary line in FIG. 2. Ambient air may be drawn through an inlet muffler 116 by the compressor 112. The compressor 112 may be driven by one or more DC motors 118 (M) that run off of DC electrical current supplied by the rechargeable battery 104 (RB). The motor 118 also preferably drives the cooling fan part of the heat exchanger 120. A variable-speed controller (VSC) or compressor motor speed controller 119, which is described in more detail below, may be integral with or separate from the control unit 110 (CU) and is preferably coupled to the motor 118 for conserving electricity consumption. The compressor 112 delivers the air under pressure to the concentrator 114. In a preferred embodiment, at a maximum speed air is delivered to the concentrator 114 at 7.3 psig nominal and may range from 6.0 to 11.8 psig. The flow rate is a minimum of 0.88 SCFM at inlet conditions of 29.92 inch Hg absolute, 70 degrees F, 50% RH.

A heat exchanger 120 may be located between the compressor 112 and the concentrator 114 to cool or heat the air to a desired temperature before entering the concentrator 114, a filter (not shown) may be located between the compressor 112 and the concentrator 114 to remove any impurities from the supply air, and a pressure transducer 122 may be located between the compressor 112 and the concentrator 114 to get a pressure reading of the air flow entering the concentrator 114.

The concentrator 114 separates oxygen gas from air for eventual delivery to the user 108 in a well-known manner. One or more of the following components may be located in a supply line 121 between the concentrator 114 and the user 108: a pressure sensor 123, a temperature sensor 125, a pump 127, a low-pressure reservoir 129, a supply valve 160, a flow and purity sensor 131, and a conservation device 190. As used herein, supply line 121 refers to the tubing, connectors, etc. used to connect the components in the line. The pump 127 may be driven by the motor 118. The oxygen gas may be stored in the low-pressure reservoir 129 and delivered therefrom via the supply line 121 to the user 108. The supply valve 160 may be used to control the delivery of oxygen gas from the low-pressure reservoir 129 to the user 108 at atmospheric pressure.

Exhaust gas may also be dispelled from the concentrator 114. In a preferred embodiment of the invention, a vacuum generator 124 (V), which may also be driven by the motor 118 and integrated with the compressor 112, draws exhaust gas from the concentrator 114 to improve the recovery and productivity of the concentrator 114. The exhaust gas may exit the system 100 through an exhaust muffler 126. A pressure transducer 128 may be located between the concentrator 114 and the vacuum generator 124 to get a pressure reading of the exhaust flow from the concentrator 114. At maximum rated speed and a flow rate of 0.78 SCFM, the pressure at the vacuum side is preferably −5.9 psig nominal and may range from −8.8 to −4.4 psig.

1. Compressor/Variable Speed Controller

Example of compressor technologies that may be used for the compressor 112 include, but not by way of limitation, rotary vane, linear piston with wrist pin, linear piston without wrist pin, nutating disc, scroll, rolling piston, diaphragm pumps, and acoustic. Preferably the compressor 112 and vacuum generator 124 are integrated with the motor 118 and are oil-less, preventing the possibility of oil or grease from entering the air flow path.

The compressor 112 preferably includes, at a minimum, a 3:1 speed ratio, with a low speed of at least 1,000 rpm and a 15,000 hour operating life when run at full speed. Operating temperature surrounding the compressor/motor system is preferably 32 to 122 degrees F. Storage temperature is preferably −4 to 140 degree F. Relative humidity is preferably 5 to 95% RH non-condensing. Voltage for the compressor 112 is preferably 12 V DC or 24V DC and the electrical power requirements are preferably less than 100 W at full speed and rated flow/nominal pressure and less than 40 W at ⅓ speed and ⅓ flow at rated pressure. A shaft mounted fan or blower may be incorporated with the compressor 112 for compressor cooling and possible complete system cooling. The maximum sound pressure level of the compressor 112 may be 46 dBA at a maximum rated speed and flow/pressure and 36 dBA at ⅓ rated speed. Preferably the compressor 112 weighs less than 3.5 pounds.

It is desirable for the compressor 112 to run at a variety of speeds, provide the required vacuum/pressure levels and flow rates, emit little noise and vibration, emit little heat, be small, not be heavy, and consume little power.

The variable-speed controller 119 is important for reducing the power consumption requirements of the compressor 112 on the rechargeable battery 104 or other energy source. With a variable-speed controller, the speed of the compressor 112 may be varied with the activity level of the user, metabolic condition of the user, environmental condition, or other condition indicative of the oxygen needs of the user as determined through the one or more output sensors 106.

For example, the variable-speed controller may decrease the speed of the motor 118 when it is determined that the oxygen requirements of the user 108 are relatively low, e.g., when the user is sitting, sleeping, at lower elevations, etc., and increased when it is determined that the oxygen requirements of the user 108 are relatively high or higher, e.g., when the user stands, when the user is active, when the user is at higher elevations, etc. This helps to conserve the life of the battery 104, reduce the weight and size of the battery 104, and reduce the compressor wear rate, improving its reliability.

One of the inventors of the present invention was a co-inventor on a variable-speed controller in the past that regulated the compressor speed to operate the compressor only at the speed and power needed to deliver oxygen at the user's prescribed flow rate. This variable-speed controller is discussed in U.S. Pat. Nos. 5,593,478 and 5,730,778, which are hereby incorporated by reference as though set forth in full.

The variable-speed controller 119 allows the compressor 112 to operate at a low average rate, typically the average rate or speed will be between full speed and ⅓ full speed of the compressor 112, resulting in an increase in battery life, decrease in battery size and weight, and decrease in compressor noise and emitted heat.

2. Concentrator

In a preferred embodiment, the concentrator 114 is an Advanced Technology Fractionator (ATF) that may be used for medical and industrial applications. The ATF may implement a pressure swing adsorption (PSA) process, a vacuum pressure swing adsorption (VPSA) process, a rapid PSA process, a very rapid PSA process or other process. If a PSA process is implemented, the concentrator may include a rotating valve or a non-rotating valve mechanism to control air flow through multiple sieve beds therein. Examples of ATF concentrators are shown and described in U.S. Pat. Nos. 5,268,021, 5,366,541, U.S. Pat. No. Re. 35,099, which are hereby incorporated by reference as though set forth in full. The sieve beds may be tapered so that they have larger diameter where gaseous flow enters the beds and a smaller diameter where gaseous flow exits the beds. Tapering the sieve beds in this manner requires less sieve material and less flow to obtain the same output.

Although an ATF concentrator 114 is used in a preferred embodiment, it will be readily apparent to those skilled in the art that other types of concentrators or air-separation devices may be used such as, but not by way of limitation, membrane separation types and electrochemical cells (hot or cold). If other types of concentrators or air-separation devices are used, it will be readily apparent to those skilled in the art that some aspects described herein may change accordingly. For example, if the air-separation device is a membrane separation type, pumps other than a compressor may be used to move air through the system.

The ATF preferably used is significantly smaller that ATFs designed in the past. The inventors of the present invention recognized that reducing the size of the ATF concentrator 114 not only made the system 100 smaller and more portable, it also improved the recovery percentage, i.e., the percentage of oxygen gas in air that is recovered or produced by the concentrator 114 and the productivity (liters per minute/lb. of sieve material) of the concentrator 114. Reducing the size of the ATF decreases the cycle time for the device. As a result, productivity is increased.

Further, the inventors also determined that finer sieve materials increased recovery rates and productivity. The time constant to adsorb unwanted gases is smaller for finer particles because the fluid path is shorter for the gases than for larger particles. Thus, fine sieve materials having small time constants are preferred. An example of a sieve material that may be used in the ATF concentrator 114 is described in U.S. Pat. No. 5,413,625 to Chao, et al., which is incorporated by reference as though set forth in full. The sieve material may be a LithiumX Zeolite that allows for a high exchange of Lithium ions. The bead size may, for example, be 0.2–0.6 mm. The Zeolite may be extruded and the structure of the sieve material may be in the form of rolled up paper.

The size of the concentrator 114 may vary with the flow rate desired. For example, the concentrator 114 may come in a 1.5 Liter per minute (LPM) size, a 2 LPM size, a 2.5 LPM size, a 3 LPM size, etc.

The oxygen gas generator 102 may also include an oxygen source in addition to the concentrator 114 such as, but not by way of limitation, a high-pressure oxygen reservoir, as described in more detail below.

An ATF valve controller 133 may be integral with or separate from the control unit 110 and is coupled with valve electronics in the concentrator 114 for controlling the valve (s) of the concentrator 114.

The concentrator may have one or more of the following energy saving modes: a sleep mode, a conserving mode, and an active mode. Selection of these modes may be done manually by the user 108 or automatically such as through the described one or more sensors 106 and control unit 110.

B. Energy Source

Figure 3:
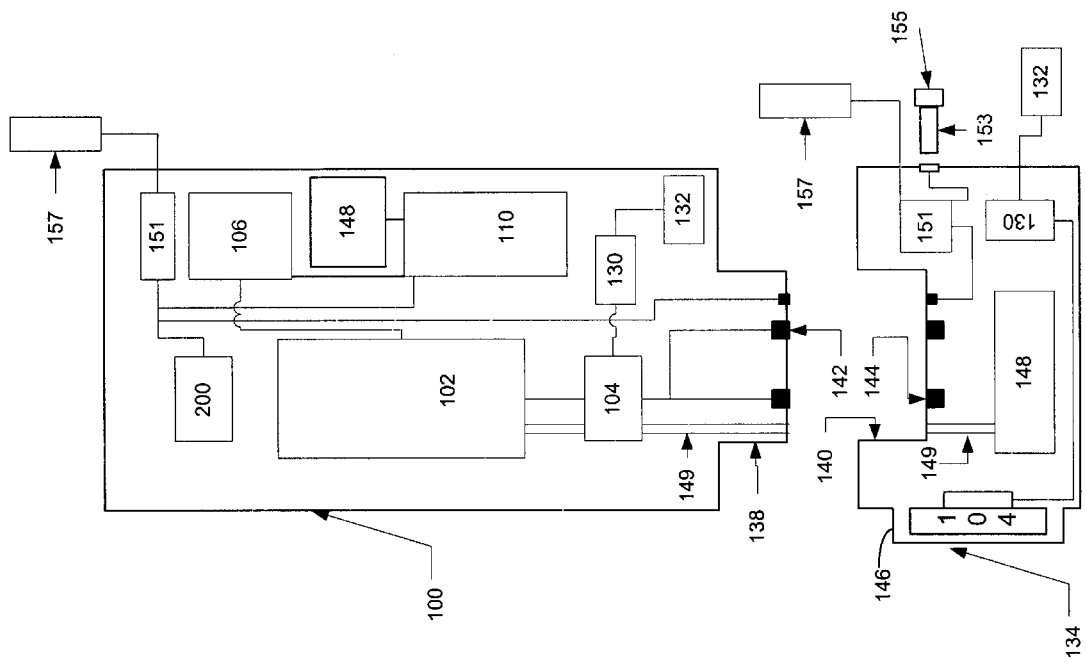
FIG. 3 is a schematic illustration of a further embodiment of the portable oxygen concentration system and an embodiment of a cradle for use with the portable oxygen concentration system.

With reference additionally to FIG. 3, in order to properly function as a lightweight, portable system 100, the system 100 must be energized by a suitable rechargeable energy source. The energy source preferably includes a rechargeable battery 104 of the lithium-ion type. It will be readily apparent to those skilled in the art that the system 100 may be powered by a portable energy source other than a lithium-ion battery. For example, a rechargeable or renewable fuel cell may be used. Although the system is generally described as being powered by a rechargeable battery 104, the system 100 may be powered by multiple batteries. Thus, as used herein, the word "battery" includes one or more batteries. Further, the rechargeable battery 104 may be comprised of one or more internal and/or external batteries. The battery 104 or a battery module including the battery 104 is preferably removable from the system 100. The system 100 may use a standard internal battery, a low-cost battery, an extended-operation internal battery, and an external secondary battery in a clip-on module.

The system 100 may have a built-in adapter including battery charging circuitry 130 and one or more plugs 132 configured to allow the system 100 to be powered from a DC power source (e.g., car cigarette lighter adapter) and/or an AC power source (e.g., home or office 110 VAC wall socket) while the battery 104 is simultaneously being charged from the DC or AC power source. The adapter or charger could also be separate accessories. For example, the adapter may be a separate cigarette lighter adapter used to power the system 100 and/or charge the battery 104 in an automobile. A separate AC adapter may be used to convert the AC from an outlet to DC for use by the system 100 and/or charging the battery 104. Another example of an adapter may be an adapter used with wheel chair batteries or other carts.

Alternatively, or in addition, a battery-charging cradle 134 adapted to receive and support the system 100 may have an adapter including battery charging circuitry 130 and a plug 132 that also allow the system 100 to be powered while the battery 104 is simultaneously being charged from a DC and/or AC power source.

The system 100 and cradle 134 preferably include corresponding mating sections 138, 140 that allow the system 100 to be easily dropped into and onto the cradle 134 for docking the system 100 with the cradle 134. The mating sections 138, 140 may include corresponding electrical contacts 142, 144 for electrically connecting the system 100 to the cradle 134.

The cradle 134 may be used to recharge and/or power the system 100 in the home, office, automobile, etc. The cradle 134 may be considered part of the system 100 or as a separate accessory for the system 100. The cradle 134 may include one or more additional charging receptacles 146 coupled to the charging circuitry 130 for charging spare battery packs 104. With a charging receptacle 146 and one or more additional battery packs 104, the user can always have a supply of additional fresh, charged batteries 104.

In alternative embodiments, the cradle 134 may come in one or more different sizes to accommodate one or more different types of systems 100.

The cradle 134 and/or system 100 may also include a humidifying mechanism 148 for adding moisture to the air flow in the system 100 through appropriate connections 149. In an alternative embodiment of the invention, the humidifying mechanism 148 may be separate from the system 100 and the cradle 134. If separate from the system 100 and cradle 134, the cradle 134 and/or system 100 may include appropriate communication ports for communicating with the separate humidifying mechanism 148. The cradle 134 may also include a receptacle adapted to receive a separate humidifying mechanism 148 for use with the system 100 when the system 100 is docked at the cradle 134.

The cradle 134 and/or system 100 may also include a telemetry mechanism or modem 151 such as a telephone modem, high-speed cable modem, RF wireless modem or the like for communicating the control unit 110 of the system 100 with one more remote computers. To this end, the cradle 135 may include a line 153 with a cable adapter or telephone jack plug 155, or a RF antenna 157. In an alternative embodiment of the invention, the telemetry mechanism or modem 151 may be separate from the cradle 134 and to this end, the cradle 134 or system 100 may include one or more appropriate communication ports, e.g., a PC port, for directly communicating the telemetry mechanism or modem 151 with the cradle 134 or system 100. For example, the cradle 134 may be adapted to communicate with a computer (at the location of the cradle) that includes the telemetry mechanism or modem 151. The computer may include appropriate software for communicating information described below using the telemetry mechanism or modem 151 with the one or more remote computers.

The telemetry mechanism or modem 151 may be used to communicate physiological information of the user such as, but not by way of limitation, heart rate, oxygen saturation, respiratory rate, blood pressure, EKG, body temperature, inspiratory/expiratory time ratio (I to E ratio) with one or more remote computers. The telemetry mechanism or modem 151 may be used to communicate other types of information such as, but not by way of limitation, oxygen usage, maintenance schedules on the system 100, and battery usage with one or more remote computers.

A user ideally uses the system 100 in its cradle 134 at home, at the office, in the automobile, etc. A user may decide to have more than one cradle, e.g., one at home, one at the office, one in the automobile, or multiple cradles at home, one in each room of choice. For example, if the user has multiple cradles 134 at home, when the user goes from room to room, e.g., from the family room to the bedroom, the user simply lifts the system 100 out of its cradle 134 in one room, and walks to the other room under battery operation. Dropping the system 100 in a different cradle 134 in the destination room restores the electrical connection between the system 100 and the AC power source. Since the system's batteries 104 are constantly charging or charged when located in the cradle 134, excursions outside the home, office, etc are as simple as going from room to room in the user's home.

Because the system 100 is small and light (2–15 pounds), the system 100 may simply be lifted from the cradle 134 and readily carried, e.g., with a shoulder strap, by an average user to the destination. If the user is unable to carry the system 100, the system 100 may be readily transported to the destination using a cart or other transporting apparatus. For an extended time away from home, office, etc., the user may bring one or more cradles 134 for use at the destination. Alternatively, in the embodiment of the system 100 including the built-in adapter, power may be drawn from power sources such as a car cigarette lighter adapter and/or an AC power outlet available at the destination. Further, spare battery packs 104 may be used for extended periods away from standard power sources.

If the battery pack 104 includes multiple batteries, the system 100 may include a battery sequencing mechanism to conserve battery life as is well known in the cellphone and laptop computer arts.

C. Output Sensor

Figure 4:
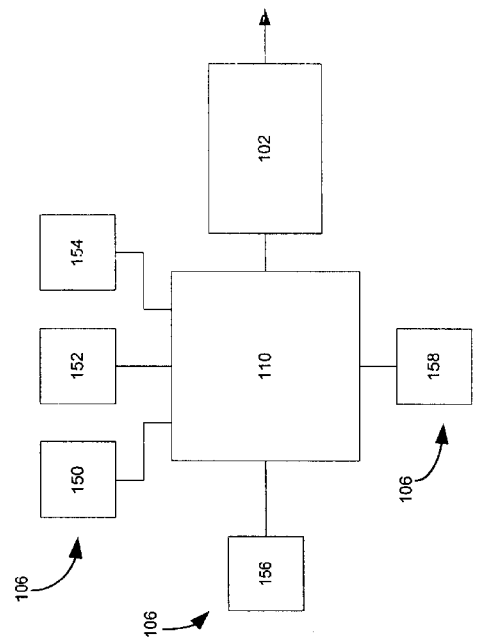
FIG. 4 is a block diagram of the one or more sensors that may be used with an embodiment of the portable oxygen concentration system.

With reference to FIGS. 1, 2 and 4, one or more output sensors 106 are used to sense one or more conditions of the user 108, environment, etc. to determine the oxygen flow rate needs of the user and, hence, the oxygen flow rate output requirements for the system 100. A control unit 110 is linked to the one or more output sensors 106 and the oxygen gas generator 102 to control the oxygen generator 102 in response to the condition(s) sensed by the one or more output sensors 106. For example, but not by way of limitation, the output sensor(s) 106 may include any or all of the activity sensors shown and described in U.S. Pat. No. 5,928,189, which is incorporated by reference as though set forth in full. These output sensors include a pressure sensor 150, a position sensor 152, an acceleration sensor 154, as well as a physiological condition or metabolic sensor 156 and an altitude sensor 158.

The first three sensors 150, 152, 154 (and, in certain circumstances, the physiological condition sensor 156) are activity sensors because these sensors provide a signal representing activity of the user 108. In the delivery of oxygen with a portable oxygen concentration system, it is important to deliver an amount of oxygen gas proportional to the activity level of the user 108 without delivering too much oxygen. Too much oxygen may be harmful for the user 108 and reduces the life of the battery 104. The control unit 110 regulates the oxygen gas generator 102 to control the flow rate of oxygen gas to the user 108 based on the one or more signals representative of the activity level of the user produced by the one or more sensors 106. For example, if the output sensor(s) 106 indicates that the user 108 has gone from an inactive state to an active state, the control unit 110 may cause the oxygen gas generator 102 to increase the flow rate of oxygen gas to the user 108 and/or may provide a burst of oxygen gas to the user 108 from a high-pressure oxygen reservoir to be described. If the output sensor(s) 106 indicates that the user 108 has gone from an active state to an inactive state, the control unit 110 may cause the oxygen gas generator 102 to reduce the flow rate of oxygen gas to the user.

In an embodiment of the invention, the amount of oxygen gas supplied is controlled by controlling the speed of the compressor motor 118 via the variable-speed controller 119.

Alternatively, or in addition to the variable-speed controller, the supply of oxygen gas may be controlled by the supply valve 160 located in the supply line 121 between the oxygen gas generator 102 and the user 108. For example, the supply valve 160 may be movable between at least a first position and a second position, the second position allowing a greater flow of concentrated gaseous oxygen through than the first position. The control unit 110 may cause the supply valve 160 to move from the first position to the second position when one or more of the activity level sensors 152, 154, 156 senses an active level of activity of the user 108. For example, the control unit 110 may include a timer, and when an active level is sensed for a time period exceeding a predetermined timed period, the control unit 110 causes the valve 160 to move from the first position to the second position.

Examples of pressure sensors 150 include, without limitation, a foot switch that indicates when a user is in a standing position compared to a sedentary position, and a seat switch that indicates when a user is in a seated position compared to a standing position.

A pendulum switch is an example of a position sensor 152. For example, a pendulum switch may include a thigh switch positioned pendulously to indicate one mode when the user is standing, i.e., the switch hangs vertically, and another mode when the user seated, i.e., the thigh switch raised to a more horizontal position. A mercury switch may be used as a position sensor.

An acceleration sensor 158 such as an accelerometer is another example of an activity sensor that provides a signal representing activity of the user.

The physiological condition or metabolic sensor 156 may also function as an activity sensor. The physiological condition sensor 156 may be used to monitor one or more physiological conditions of the user for controlling the oxygen gas generator 102 or for other purposes. Examples of physiological conditions that may be monitored with the sensor 156 include, but without limitation, blood oxygen level, heart rate, respiration rate, blood pressure, EKG, body temperature, and I to E ratio. An oximeter is an example of a sensor that is preferably used in the system 100. The oximeter measures the blood oxygen level of the user, upon which oxygen production may be at least partially based.

An altitude sensor 158 is an example of an environmental or ambient condition sensor that may sense an environmental or ambient condition upon which control of the supply of oxygen gas to the user may be at least partially based. The altitude sensor 158 may be used alone or in conjunction with any or all of the above sensors, the control unit 110 and the oxygen gas generator 102 to control the supply of oxygen gas to the user in accordance with the sensed altitude or elevation. For example, at higher sensed elevations, where air is less concentrated, the control unit may increase the flow rate of oxygen gas to the user 108 and at lower sensed elevations, where air is more concentrated, the control unit may decrease the flow rate of oxygen gas to the user 108 or maintain it at a control level.

It will be readily apparent to those skilled in the art that one or more additional or different sensors may be used to sense a condition upon which control of the supply of oxygen gas to the user may be at least partially based. Further, any or all of the embodiments described above for regulating the amount of oxygen gas supplied to the user 108, i.e., variable-speed controller 119, supply valve 160, (or alternative embodiments) may be used with the one or more sensors and the control unit 110 to control of the supply of oxygen gas to the user 108.

D. Control Unit

Figure 5:
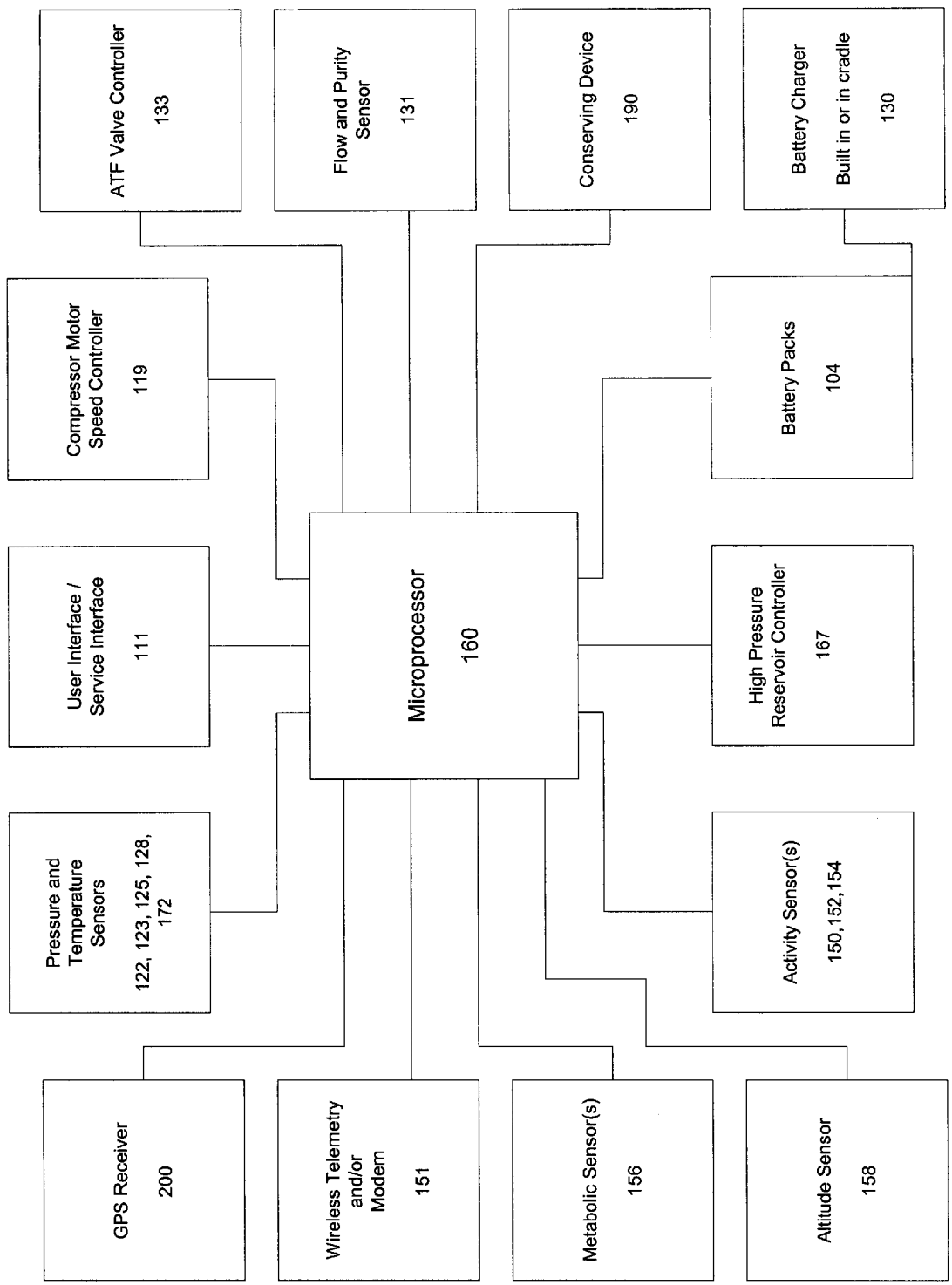
FIG. 5 is a block diagram of the one or more components that may be controlled by the control unit of the portable oxygen concentration system.

With reference to FIG. 5, the control unit 110 may take any well-known form in the art and includes a central microprocessor or CPU 160 in communication with the components of the system described herein via one or more interfaces, controllers, or other electrical circuit elements for controlling and managing the system. The system 100 may include a user interface 111 (FIG. 5) as part of the control unit 110 or coupled to the control unit 110 for allowing the user, provider, doctor, etc. to enter information, e.g., prescription oxygen level, flow rate, activity level, etc., to control the system 100.

The main elements of an embodiment of the system 100 have been described above. The following sections describe a number of additional features, one or more of which may be incorporated into the embodiments of the invention described above as one or more separate embodiments of the invention.

II. Conserving Device

Figure 6:
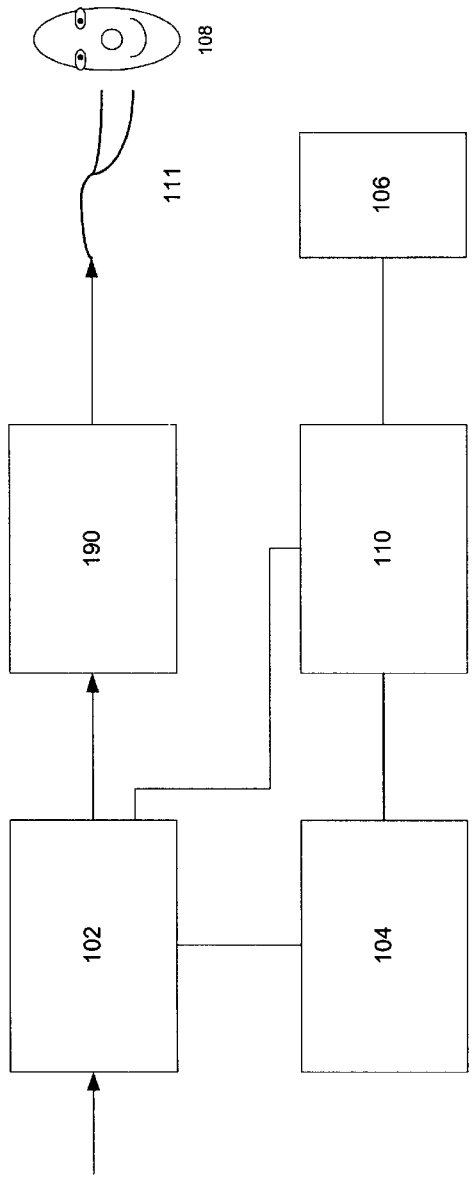
FIG. 6 is a block diagram of a portable oxygen concentration system constructed in accordance with additional embodiment of the invention.

With reference to FIG. 6, a conserving device or demand device 190 may be incorporated into the system 100 to more efficiently utilize the oxygen produced by the oxygen gas generator 102. During normal respiration, a user 108 inhales for about one-third of the time of the inhale/exhale cycle and exhales the other two-thirds of the time. Any oxygen flow provided to the user 108 during exhalation is of no use to the user 108 and, consequently, the additional battery power used to effectively provide this extra oxygen flow is wasted. A conserving device 190 may include a sensor that senses the inhale/exhale cycle by sensing pressure changes in the cannula 111 or another part of the system 100, and supply oxygen only during the inhale portion or a fraction of the inhale portion of the breathing cycle. For example, because the last bit of air inhaled is of no particular use because it is trapped between the nose and the top of the lungs, the conserving device 190 may be configured to stop oxygen flow prior to the end of inhalation, improving the efficiency of the system 100. Improved efficiency translates into a reduction in the size, weight, cost and power requirements of the system 100.

The conserving device 190 may be a stand-alone device in the output line of the system 100, similar to a regulator for scuba diving, or may be coupled to the control unit 110 for controlling the oxygen generator 102 to supply oxygen only during inhalation by the user 108.

The conserving device 190 may include one or more of the sensors described above. For example, the conserving device may include a sensor for monitoring the respiration rate of the user.

The system 100 may also include a special cannula retraction device for retracting the cannula 111 when not in use. Further, the cannula 111 may come in different lengths and sizes.

III. High-pressure Reservoir

Figure 7:
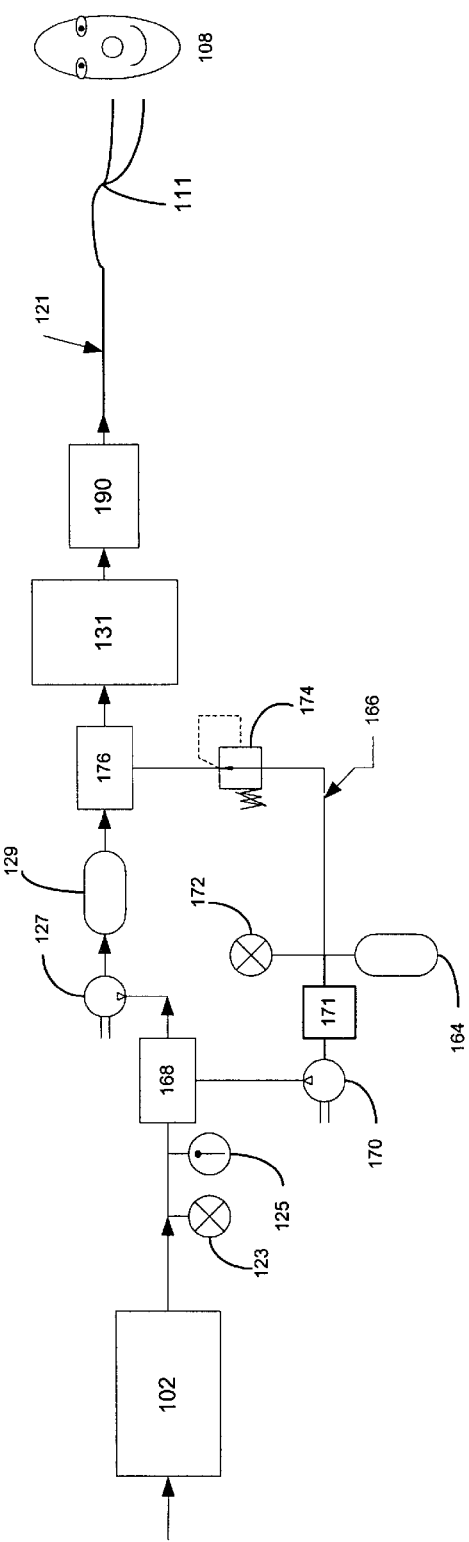
FIG. 7 is a schematic illustration of another embodiment of a portable oxygen concentration system including a high-pressure reservoir.

With reference to FIG. 7, a high-pressure reservoir 164 may be located in a secondary line 166 for delivering an additional supply of oxygen gas to the user 108 when the oxygen gas generator 102 can not meet the oxygen gas demands of the user 108. Any of the components described below in the secondary line 166 may be coupled to the control unit 110 or a high-pressure reservoir controller 167 (FIG. 5) for control thereby. Exemplary situations where this additional oxygen gas need may occur are when a user suddenly goes from an inactive state to an active state, e.g., when getting out of a chair, when the system 100 is turned on, or when the system 100 goes from a conserving mode or sleep mode to an active mode. As used herein, secondary line 166 refers to the tubing, connectors, etc. used to connect the components in the line. A valve 168 may be controlled by the control unit 110 to allow gaseous oxygen to flow into the secondary line 166. The valve 168 may be configured to allow simultaneous flow to both the supply line 121 and the secondary line 166, flow to only the supply line 121, or flow to only the secondary line 166.

A pump or compressor 168, which is preferably powered by the motor 118, delivers the oxygen gas at a relatively high pressure, e.g., at least approximately 100 psi, to the high-pressure reservoir 164.

An oxygen-producing electrochemical cell 171 may be used in conjunction with or instead of the elements described in the secondary line 166 to supply additional oxygen gas to the user 108. U.S. Pat. No. 6,010,317 to Maget, et al., which is incorporated by reference as though set forth in full, describes an electrochemical cell that may be used for this purpose. For example the electrochemical cell 171 may be used to deliver oxygen gas at a relatively high pressure to the high-pressure reservoir 164.

A pressure sensor 172 is in communication with the high-pressure reservoir 164 and the control unit 110 so that when the pressure in the high-pressure reservoir 164 reaches a certain limit, the control unit 110 causes the valve 168 to direct oxygen to the secondary line 166.

A regulator 174 may be used to control flow and reduce pressure of the oxygen gas to the user 108.

A valve 176 may also be controlled by the control unit 110 to allow gaseous oxygen from the high-pressure reservoir 164 to flow into the supply line 121 when the user 108 requires an amount of oxygen gas that can not be met by the oxygen gas generator 102. The valve 176 may be configured to allow simultaneous flow from the oxygen gas generator 102 and the high-pressure reservoir 164, from only the oxygen gas generator 102, or from only the high-pressure reservoir 164.

The one or more sensors 106 are interrelated with the control unit 110 and the oxygen gas generator 102 so as to supply an amount of oxygen gas equivalent to the oxygen gas needs of the user 108 based at least in part upon one or more conditions sensed by the one or more sensors 106. When the oxygen gas generator 102 can not meet the oxygen gas demands of the user 108, the control unit 110, based at least in part upon sensing one or more conditions indicative of the oxygen needs of the user, may cause the high-pressure reservoir 164 (via the valve 176) to supply the additional oxygen gas needed.

In the scenario where the oxygen gas generator 102 is capable of supplying the full oxygen gas needs of the user 108, but is simply turned off or is in a conserving or sleep mode, the period of time that the high-pressure reservoir 164 supplies the oxygen gas, i.e., the period of time that the valve 176 connects the high-pressure reservoir 164 with the supply line 121, is at least as long as the time required for the oxygen gas generator 102 to go from an off or inactive condition to an on or active condition.

In another scenario, the control unit 110 may cause oxygen gas to be supplied to the user from the high-pressure reservoir 164 when the demand for gaseous oxygen by the user exceeds the maximum oxygen gas output of the oxygen gas generator 102. Although the high-pressure reservoir 164 is shown and described as being filled by the oxygen gas generator 102, in an alternative embodiment, the high-pressure reservoir 164 may be filled by a source outside or external to the system.

IV. Global Positioning System

With reference back to FIG. 3, in an alternative embodiment of the invention, the system 100 may include a global positioning system (GPS) receiver 200 for determining the location of the system 100. The location of the receiver 200 and, hence, the user 108 can be transmitted to a remote computer via the telemetry mechanism or modem 151. This may be desirable for locating the user 108 in the event the user has a health problem, e.g., heart attack, hits a panic button on the system, an alarm is actuated on the system, or for some other reason.

V. Additional Options and Accessories

In addition to the cradle 134, the portable oxygen concentration system 100 may include additional options and accessories. A number of different types of bags and carrying cases such as, but not by way of limitation, a shoulder bag, a backpack, a fanny pack, a front pack, and a split pack in different colors and patterns may be used to transport the system 100 or other system accessories. A cover may be used to shield the system from inclement weather or other environmental damage. The system 100 may also be transported with a rolling trolley/cart, a suit case, or a travel case. The travel case may be designed to carry the system 100 and include enough room to carry the cannulae 111, extra batteries, an adapter, etc. Examples of hooks, straps, holders for holding the system 100 include, but not by way of limitation, hooks for seatbelts in cars, hooks/straps for walkers, hooks/straps, for wheel chairs, hooks/straps for hospital beds, hooks for other medical devices such as ventilators, hooks/straps for a golf bag or golf cart, hooks/straps for a bicycle, and a hanging hook. The system 100 may also include one or more alarm options. An alarm of the system 100 may be actuated if, for example, a sensed physiological condition of the user 108 falls outside a pre-defined range. Further, the alarm may include a panic alarm that may be manually actuated by the user 108. The alarm may actuate a buzzer or other sounding device on the system 100 and/or cause a communication to be sent via the telemetry mechanism or modem 151 to another entity, e.g., a doctor, a 911 dispatcher, a caregiver, a family member, etc.

Although this invention has been described in terms of certain preferred embodiments, other embodiments apparent to those of ordinary skill in the art are also within the scope of this invention. Accordingly, the scope of this invention is intended to be defined only by the claims that follow.

What is claimed is:

1. A portable oxygen concentrator system adapted to be readily transported by a user, comprising:
   an internal renewable energy source;
   an air separation device powered by said energy source and adapted to convert ambient air into concentrated oxygen gas for said user, the air separation device including a pump and an oxygen concentrator, the pump adapted to supply ambient air to said oxygen concentrator and said oxygen concentrator adapted to separate concentrated gaseous oxygen from supplied ambient air and including a plurality of absorber columns and a rotating valve, the rotating valve relatively rotatable with respect to the plurality of absorber columns to provide valving action for selectively transferring fluids through the plurality of absorber columns for converting ambient air into concentrated oxygen gas for said user,
   wherein said portable oxygen concentrator system weight 2–15 pounds.

2. The portable oxygen concentration system of claim 1, wherein said energy source is a fuel cell.

3. The portable oxygen concentration system of claim 1, wherein said pump includes a compressor adapted to compress and supply ambient air to said oxygen concentrator.

4. The portable oxygen concentration system of claim 3, wherein the concentrator is a pressure swing adsorption (PSA) concentrator.

5. The portable oxygen concentration system of claim 3, wherein the concentrator is a vacuum pressure swing adsorption (VPSA) concentrator, said system including a vacuum generator adapted to draw exhaust gas from concentrator to improve the recovery and productivity of the concentrator.

6. The portable oxygen concentration system of claim 3, wherein the concentrator is a rapid PSA concentrator.

7. The portable oxygen concentration system of claim 3, wherein the concentrator is a very rapid PSA concentrator.

8. The portable oxygen concentration system of claim 1, wherein the concentrator is a membrane separation concentrator.

9. The portable oxygen concentration system of claim 1, wherein the concentrator is an electrochemical cell concentrator.

10. The portable oxygen concentration system of claim 3, further including at least one sensor adapted to sense one or more conditions indicative of the oxygen gas needs of said user, and a control unit interrelated with said air separation device, said second concentrated oxygen source, and said at least one sensor so as to supply an amount of oxygen gas equivalent to the oxygen gas needs of said user based at least in part upon the one or more conditions sensed by said at least one sensor and cause oxygen gas from the second concentrated oxygen gas source to supplement the oxygen gas supplied from the air separation device when the demand for oxygen gas exceeds the supply capacity of the air separation device, wherein the compressor is a variable-speed compressor and said control unit is adapted to control the concentrator so as to supply an amount of oxygen gas equivalent to the oxygen gas needs of said user by controlling the speed of said variable-speed compressor based at least in part upon the one or more conditions sensed by said at least one sensor.

11. The potable oxygen concentration system of claim 1, further including at least one sensor adapted to sense one or more conditions indicative of the oxygen gas needs of said user, and a control unit interrelated with said air separation device, said second concentrated oxygen source, and said at least one sensor so as to supply an amount of oxygen gas equivalent to the oxygen gas needs of said user based at least in part upon the one or more conditions sensed by said at least one sensor and cause oxygen gas from the second concentrated oxygen gas source to supplement the oxygen gas supplied from the air separation device when the demand for oxygen gas exceeds the supply capacity of the air separation device, wherein said at least one sensor includes a metabolic sensor adapted to sense a metabolic condition of the user, said control unit interrelated with said air separation device and said metabolic sensor to control the air separation device so as to supply an amount of oxygen gas equivalent to the oxygen gas needs of said user based at least in part upon the metabolic condition sensed by said at least one sensor.

12. The portable oxygen concentration system of claim 11, wherein said metabolic sensor is an oximeter.

13. The portable oxygen concentration system of claim 11, wherein said metabolic sensor is adapted to measure at least one of heart rate, oxygen saturation, respiratory rate, blood pressure, EKG, body temperature, inspiratory/expiratory time ratio.

14. The portable oxygen concentration system of claim 1, further including at least one sensor adapted to sense one or more conditions indicative of the oxygen gas needs of said user, and a control unit interrelated with said air separation device, said second concentrated oxygen source, and said at least one sensor so as to supply an amount of oxygen gas equivalent to the oxygen gas needs of said user based at least in part upon the one or more conditions sensed by said at least one sensor and cause oxygen gas from the second concentrated oxygen gas source to supplement the oxygen gas supplied from the air separation device when the demand for oxygen gas exceeds the supply capacity of the air separation device, wherein said at least one sensor includes an environmental condition sensor adapted to sense an environment or ambient condition in the environment of said user, said control unit interrelated with said air separation device and said environmental condition sensor to control the air separation device so as to supply an amount of oxygen gas equivalent to the oxygen gas needs of said user based at least in part upon the environmental condition sensed by said environmental condition sensor.

15. The portable oxygen concentration system of claim 1, further including at least one sensor adapted to sense one or more conditions indicative of the oxygen gas needs of said user, and a control unit interrelated with said air separation device, said second concentrated oxygen source, and said at least one sensor so as to supply an amount of oxygen gas equivalent to the oxygen gas needs of said user based at least in part upon the one or more conditions sensed by said at least one sensor and cause oxygen gas from the second concentrated oxygen gas source to supplement the oxygen gas supplied from the air separation device when the demand for oxygen gas exceeds the supply capacity of the air separation device, wherein said at least one sensor includes an activity level sensor adapted to sense a level of activity of said user, said control unit interrelated with said air separation device and said activity level sensor t(control the air separation device so as to supply an amount of oxygen gas equivalent to the oxygen gas needs of said user based at least in part upon the level of activity of the user sensed by said activity level sensor.

16. The portable oxygen concentration system of claim 15, wherein said activity level sensor is a member selected from the group of a pressure sensor, a position sensor, and an acceleration sensor.

17. The portable oxygen concentration system of claim 1, further including a second concentrated oxygen source separate from the air separation device to supplement the supply of concentrated oxygen gas from the air separation device, at least one sensor adapted to sense one or more conditions indicative of the oxygen gas needs of said user, and a control unit interrelated with said air separation device, said second concentrated oxygen source, and said at least one sensor so as to supply an amount of oxygen gas equivalent to the oxygen gas needs of said user based at least in part upon the one or mote conditions sensed by said at least one sensor and cause oxygen gas from the second concentrated oxygen gas source to supplement the oxygen gas supplied from the air separation device when the demand for oxygen gas exceeds the supply capacity of the air separation device, wherein the second concentrated oxygen source is a high-pressure reservoir adapted to supply oxygen gas, said control unit interrelated with said high-pressure reservoir and said at least one sensor to cause said high-pressure reservoir to supply oxygen gas to said user based at least in part upon one or more conditions sensed by said at least one sensor.

18. The portable oxygen concentration system of claim 17, wherein said high-pressure reservoir is adapted to supply oxygen gas at least as long as the time required for said air separation device to supply the full oxygen gas needs of said user.

19. The portable oxygen concentration system of claim 17, wherein said control unit is adapted to cause oxygen gas to be supplied to said user from said high-pressure reservoir when the demand for gaseous oxygen by said user exceeds the supply capacity of said air separation device.

20. The portable oxygen concentration system of claim 17, wherein said high-pressure reservoir is adapted to be filled by said air separation device.

21. The portable oxygen concentration system of claim 17, wherein said high-pressure reservoir is adapted to be filled by an oxygen source external to the system.

22. The portable oxygen concentration system of claim 17, wherein said high-pressure reservoir is adapted to be filled by an electrochemical cell capable of producing concentrated oxygen gas.

23. The portable oxygen concentration system of claim 1, further including at least one sensor adapted to sense one or more conditions indicative of the oxygen gas needs of said user, and a control unit interrelated with said air separation device, said second concentrated oxygen source, and said at least one sensor so as to supply an amount of oxygen gas equivalent to the oxygen gas needs of said user based at least in part upon the one or more conditions sensed by said at least one sensor and cause oxygen gas from the second concentrated oxygen gas source to supplement the oxygen gas supplied from the air separation device when the demand for oxygen gas exceeds the supply capacity of the air separation device, wherein said system includes a supply valve, said valve movable between at least a first position and a second position, said second position allowing a greater flow of concentrated gaseous oxygen through than said first position, and said control unit adapted to cause said valve to move from said first position to said second position based at least in part upon one or more conditions sensed by said at least one sensor.

24. The portable oxygen concentration system of claim 23, wherein solid control unit includes a timer, at least one sensor sensor coupled to said timer so that when one or more conditions sensed exceeds a timed period, said control unit causes said valve to move from the first position to the second position.

25. The portable oxygen concentration system of claim 1, further including a gaseous oxygen conservation device in communication with said air separation device and adapted to conserve the oxygen gas flow to said user by allowing oxygen gas flow only upon inhalation by said user.

26. The portable oxygen concentration system of claim 25, wherein said gaseous oxygen conservation device is adapted to allow oxygen gas flow only upon a portion of the inhalation cycle.

27. The portable oxygen concentration system of claim 1, wherein the air separation device is a pressure swing adsorption (PSA) concentrator including a LithiumX Zeolite sieve material.

28. The portable oxygen concentration system of claim 1, wherein said system includes a GPS receiver for locating the geographical location of the system.

29. The portable oxygen concentration system of claim 1, wherein the power consumption of the system in an active mode is less than 100 watts and in a conservation mode is less than 40 watts.

30. The portable oxygen concentration system of claim 1, wherein the noise produced by operation of the system is less than 36 dBA at one meter distance when the system is in a conservation mode and is less than 46 dBA at one meter distance when the system is in an active mode.

31. The portable oxygen concentration system of claim 1, wherein said energy source is a rechargeable battery.

32. The portable oxygen concentration system of claim 31, further including a cradle adapted to receive said portable oxygen concentration system and to couple said system to an external energy source for at least one of charging said rechargeable battery and powering said system.

33. The portable oxygen concentration system of claim 32, wherein said, wherein said cradle includes a telemetry mechanism adapted to communicate said system with a remote computer for communicating information related to at least one of said portable oxygen concentration system and said user.

34. The portable oxygen concentration system of claim 32, wherein said cradle includes a humidifier for adding moisture to an air flow path of said system.

35. A method of supplying gaseous oxygen to a user using a portable oxygen concentrator system that is readily transported by said user, comprising:

providing a portable oxygen concentrator system that is readily transportable by a user, the portable oxygen concentrator system comprising: an internal renewable energy source, an air separation device powered by said renewable energy source to convert ambient air into concentrated oxygen gas for said user, the air separation device including a plurality of adsorber columns and a rotating valve, the rotating valve relatively rotatable with respect to the plurality of adsorber columns to provide valving action for selectively transferring fluids through the plurality of adsorber columns for converting ambient air into concentrated oxygen gas for said user, at least one sensor to sense one or more conditions indicative of the oxygen gas needs of said user, and a control unit interrelated with said air separation device and said at least one sensor to control the air separation device so as to supply an amount of oxygen gas equivalent to the oxygen gas needs of said user based at least in part upon the one or more conditions sensed by said at least one sensor, said portable oxygen concentrator system weighing 2–15 pounds;

sensing one or more conditions indicative of the oxygen gas needs of said user with said at least one sensor;

controlling said air separation device to operate in at least an active mode and a conservation mode, the air separation device converting ambient air into concentrated oxygen gas and supplying an amount of concentrated oxygen gas equivalent to the oxygen gas needs of said user based upon the one or more conditions sensed by said at least one sensor, the rotating valve relatively rotating with respect to the plurality of absorber columns to provide valving action for selectively transferring fluids through the plurality of adsorber columns for converting ambient air into concentrated oxygen gas for said user.

36. A method of supplying gaseous oxygen to a user using a portable oxygen concentrator system that is readily transported by said user, comprising:

providing a portable oxygen concentrator system that is readily transportable by a user, the portable oxygen concentrator system comprising: an internal renewable energy source, a vacuum pressure swing adsorption concentrator including a plurality of adsorber columns and a rotating valve, the rotating valve relatively rotatable with respect to the plurality of adsorber columns to provide valving action for selectively transferring fluids through the plurality of absorber columns for converting ambient air into concentrated oxygen gas for said user, a compressor to compress and supply ambient air to said vacuum pressure swing adsorption concentrator and draw exhaust gas from the vacuum pressure swing adsorption concentrator to improve the recovery and productivity of the vacuum pressure swing adsorption concentrator, the vacuum pressure swing adsorption concentrator and compressor powered by said renewable energy source, at least one sensor to sense one or more conditions indicative of the oxygen gas needs of said user, and a control unit interrelated with at least one of said vacuum pressure swing adsorption concentrator, compressor and said at least one sensor so as to supply an amount of oxygen gas equivalent to the oxygen gas needs of said user based at least in part upon the one or more conditions sensed by said at least one sensor, the portable oxygen concentrator system weighing 2–15 pounds;

sensing one or more conditions indicative of the oxygen gas needs of said user with at least one sensor;

compressing and supplying ambient air to said vacuum pressure swing adsorption concentrator with said compressor;

drawing exhaust gas from the vacuum pressure swing adsorption concentrator to improve the recovery and productivity of the vacuum pressure swing adsorption concentrator with said compressor; and controlling said vacuum pressure swing adsorption concentrator to operate in at least an active mode and a conservation mode, the vacuum pressure swing adsorption concentrator converting ambient air into concentrated oxygen gas and supplying an amount of concentrated oxygen gas equivalent to the oxygen gas needs of said user based upon the one or more conditions sensed by said at least one sensor, the rotating valve relatively rotating with respect to the plurality of adsorber columns to provide valving action for selectively transferring fluids through the plurality of adsorber columns for converting ambient air into concentrated oxygen gas for said user.

37. A method of supplying gaseous oxygen to a user using a portable oxygen concentrator system that is readily transported by said user, comprising:

providing a portable oxygen concentrator system that is readily transportable by a user, the portable oxygen concentrator system comprising: an internal renewable energy source, an air separation device powered by said energy source and adapted to convert ambient air into concentrated oxygen gas for said user, the air separation device including a pump and an oxygen concentrator, the pump adapted to supply ambient air to said oxygen concentrator and said oxygen concentrator adapted to separate concentrated gaseous oxygen from the supplied ambient air and including a plurality of adsorber columns and a rotating valve, the rotating valve relatively rotatable with respect to the plurality of adsorber columns to provide valving action for selectively transferring fluids through the plurality of adsorber columns for converting ambient air into concentrated oxygen gas for said user, at least one sensor adapted to sense one or more conditions indicative of the oxygen gas needs of said user, and a control unit interrelated with said air separation device and said at least one sensor so as to supply an amount of oxygen gas equivalent to the oxygen gas needs of said user based at least in part upon the one or more conditions sensed by said at least one sensor, said portable oxygen concentrator system weighing 2–15 pounds;

sensing one or more conditions indicative of the oxygen gas needs of said user with at least one sensor;

controlling the air-separation device to convert ambient air into concentrated oxygen gas and supply an amount of concentrated oxygen gas equivalent to the oxygen gas needs of said user based upon the one or more conditions sensed by said at least one sensor, the rotating valve relatively rotating with respect to the plurality of adsorber columns to provide valving action for selectively transferring fluids through the plurality of adsorber columns for converting ambient air into concentrated oxygen gas for said user.

38. The method of claim 37, wherein ambient air is converted into concentrated oxygen gas by a pressure swing adsorption (PSA) process.

39. The method of claim 37, wherein ambient air is converted into concentrated oxygen gas by a vacuum pressure swing adsorption (VPSA) process.

40. The method of claim 37, wherein ambient air is converted into concentrated oxygen gas by a rapid PSA process.

41. The method of claim 37, wherein ambient air is converted into concentrated oxygen gas by a very rapid PSA process.

42. The method of claim 37, wherein ambient air is converted into concentrated oxygen gas by a membrane separation process.

43. The method of claim 37, wherein ambient air is converted into concentrated oxygen gas by an electrochemical process.

44. The method of claim 37, wherein said air-separation device includes: a variable-speed compressor and a concentrator, the step of controlling an air-separation device includes controlling the speed of said variable-speed compressor based at least in part upon the one or more conditions sensed by said at least one sensor to supply an amount of concentrated oxygen gas with said concentrator equivalent to the oxygen gas needs of said user.

45. The method of claim 37, wherein the step of sensing includes sensing one or more metabolic conditions of said user, and the step of controlling includes controlling an air-separation device to convert ambient air into concentrated oxygen gas and supply an amount of concentrated oxygen gas equivalent to the oxygen gas needs of said user based upon the one or more metabolic conditions sensed by said at least one sensor.

46. The method of claim 45, wherein the step of sensing includes sensing an oxygen level in the user with an oximeter.

47. The method of claim 45, wherein the step of sensing includes sensing a heart rate of the user.

48. The method of claim 45, wherein the step of sensing includes sensing a respiratory rate of the user.

49. The method of claim 45, wherein the step of sensing includes sensing blood pressure of the user.

50. The method of claim 45, wherein the step of sensing includes sensing an EKG of the user.

51. The method of claim 45, wherein the step of sensing includes sensing body temperature of the user.

52. The method of claim 45, wherein the step of sensing includes sensing an inspiratory/expiratory time ratio of the user.

53. The method of claim 37, wherein the step of sensing includes sensing one or more environmental or ambient conditions in the environment of said user, and the step of controlling includes controlling an air-separation device to convert ambient air into concentrated oxygen gas and supply an amount of concentrated oxygen gas equivalent to the oxygen gas needs of said user based upon the one or more environmental or ambient conditions sensed by said at least one sensor.

54. The method of claim 53, wherein the step of sensing includes sensing the altitude of the portable oxygen concentration system.

55. The method of claim 37, wherein the step of sensing includes sensing a level of activity of said user, and the step of controlling includes controlling an air-separation device to convert ambient air into concentrated oxygen gas and supply an amount of concentrated oxygen gas equivalent to the oxygen gas needs of said user based upon the level of activity sensed by said at least on e sensor.

56. The method of claim 55, wherein the step of sensing includes sensing a pressure exerted by said user when sitting or a lack or pressure when said user is upright.

57. The method of claim 55, wherein the step of sensing includes sensing an position of said user.

58. The method of claim 55, wherein the step of sensing includes sensing an acceleration of said user.

59. The method of claim 37, further including a second concentrated oxygen source separate from the air separation device to supplement the supply of concentrated oxygen gas from the air separation device and the second concentrated oxygen source is a high-pressure reservoir.

60. The method of claim 59, further including the step of controlling said high-pressure reservoir to supply oxygen gas to said user based at least in part upon one or more conditions sensed by said at least one sensor.

61. The method of claim 59, wherein the step of supplying includes supplying additional oxygen gas with a high-pressure reservoir at least as long as the time required for said air separation device to supply the full oxygen gas needs of said user.

62. The method of claim 59, wherein the step of supplying includes supplying additional oxygen gas with a high-pressure reservoir when the demand for gaseous oxygen by said user exceeds the supply capacity of said air separation device.

63. The method of claim 59, further including the step of filling the high-pressure reservoir with said air separation device.

64. The method of claim 59, further including the step of filling the high-pressure reservoir with an oxygen source external to the system.

65. The method of claim 59, further including the step of filling the high-pressure reservoir with an electrochemical cell capable of producing concentrated oxygen gas.

66. The method of claim 37, wherein said system includes a supply valve, the method further including the step of moving said valve between at least a first position and a second position based at least in part upon one or more conditions sensed by said at least one sensor, said second position allowing a greater flow of concentrated gaseous oxygen through than said first position.

67. The method of claim 66, further including the step of moving said valve from the first position to the second position when one or more conditions sensed exceeds a predetermined timed period.

68. The method of claim 37, further including the step of conserving the oxygen gas flow to said user by allowing oxygen gas flow only upon inhalation by said user.

69. The method of claim 37, wherein the internal renewable energy source includes one or more rechargeable batteries, and the method further including the steps of docking the portable oxygen concentration system in a cradle and charging the one or more rechargeable batteries of the portable oxygen concentration system with a charger in the cradle.

70. The method of claim 37, further including the step of communicating information related to at least one of said portable oxygen concentration system and slid user with a remote computer using a telemetry mechanism in said cradle.

71. The method of claim 37, further including the step of adding moisture to an air flow path of said portable oxygen concentration system using a humidifier in said cradle.

72. The method of claim 37, further including locating the geographical location of said portable oxygen concentration system using a GPS in said portable oxygen concentration system.

* * * * *